United States Patent [19]

McCarthy et al.

[11] Patent Number: 5,538,723

[45] Date of Patent: Jul. 23, 1996

[54] METHOD FOR SUPPRESSING THE VISCOSITY OF BIOINSECTICIDE SLURRIES AND RELATED SLURRIES

[75] Inventors: Kevin J. McCarthy, St. Louis; Charles W. Burkhardt, Fenton; Steven P. Holmes, St. Louis, all of Mo.; David J. Poelker, Belleville, Ill.

[73] Assignee: Petrolite Corporation, St. Louis, Mo.

[21] Appl. No.: 205,057

[22] Filed: Mar. 2, 1994

[51] Int. Cl.$^6$ .............................. A61K 38/00; A01N 63/02
[52] U.S. Cl. .................................... 424/115; 424/93.1
[58] Field of Search ..................... 424/409, 93.1, 424/115, 236.1, 261.1

[56] References Cited

U.S. PATENT DOCUMENTS

| | | | |
|---|---|---|---|
| 3,709,815 | 1/1973 | Boothe | 210/58 |
| 3,709,816 | 1/1973 | Walker | 210/58 |
| 3,928,196 | 12/1975 | Persinski et al. | 210/58 |
| 4,015,991 | 4/1977 | Persinski et al. | 106/90 |
| 4,147,632 | 4/1979 | Yada et al. | 260/29.6 |
| 4,219,498 | 8/1980 | Doi et al. | 260/513 N |
| 4,293,427 | 10/1981 | Lucas et al. | 252/8.5 C |
| 4,319,014 | 3/1982 | Peascoe et al. | 526/287 |
| 4,342,653 | 8/1982 | Halverson | 210/734 |
| 4,357,245 | 11/1982 | Engelhardt et al. | 252/8.5 C |
| 4,552,665 | 11/1985 | Ralston et al. | 210/697 |
| 5,061,697 | 10/1991 | Sasha et al. | 424/409 |
| 5,252,321 | 10/1993 | Huth et al. | 424/78.32 |
| 5,319,093 | 6/1994 | Huth et al. | 548/308 |

FOREIGN PATENT DOCUMENTS

| 8607877 | 10/1988 | WIPO | 424/409 |
|---|---|---|---|

OTHER PUBLICATIONS

Rohm and Haas Company, ACRYSOL® QR-1086, Calcium Phosphate Stabilizer, Dec. 1986.
Merck Index 11th Ed. Abstract 3870.

*Primary Examiner*—Peter F. Kulkosky
*Attorney, Agent, or Firm*—Kenneth Solomon

[57] ABSTRACT

A method for suppressing the viscosity of a calcium exotoxin slurry is disclosed. The method comprises adding to the slurry a viscosity-suppressing amount of a copolymer of a vinyl-based monomer and 2-acrylamide-2-methylpropane sulfonic acid or its sodium salt. The copolymer has a weight average molecular weight of from about 1,000 to about 10,000. A slurry comprising calcium exotoxin and about 0.25 to about 2.5 percent by weight of such copolymer is also disclosed.

20 Claims, No Drawings

METHOD FOR SUPPRESSING THE VISCOSITY OF BIOINSECTICIDE SLURRIES AND RELATED SLURRIES

BACKGROUND OF THE INVENTION

1. Field of the Invention

The present invention relates to the suppression of viscosity in calcium exotoxin slurries and more particularly to the suppression of viscosity of such slurries by the addition thereto of certain copolymeric additives.

2. Description of Prior Art

In the latter stages of processing of various bioinsecticides by conventional techniques, a calcium exotoxin slurry is formed. This slurry contains, in addition to the desired calcium exotoxin bioinsecticide product, fermentation by-products, water, biomass, and various oils that served as food nutrients. The slurry then is concentrated by driving off water, often by ultrafiltration, to produce a product of lower water concentration and that is less expensive to transport. However, the viscosity of the slurry builds dramatically as water is driven off. Therefore, the degree of concentration that can be obtained without rendering the slurry too viscous to be worked practically is limited severely. The slurries rapidly become too viscous to be pumped or otherwise processed easily or conveniently.

As a result, the industry has been seeking a way to increase the concentration of such slurries further without increasing the viscosity thereof to unmanageable levels. Various chemical additives for reducing or suppressing viscosity have been tried, but none have been found to be sufficiently effective in reducing or suppressing the viscosity of the slurry. Accordingly, the industry also has been searching for a method for concentrating the slurry without increasing the viscosity to unmanageable levels that does not involve compositions or techniques that result in the frequent fouling of the ultrafiltration membranes that often are used to remove water from the slurry.

SUMMARY OF THE INVENTION

The present invention, therefore, is directed to a novel method for suppressing the viscosity of a calcium exotoxin slurry. The method comprises adding to the slurry a viscosity-suppressing amount of a copolymer of (1) acrylic acid, methacrylic acid, maleic acid, the sodium salt of any of such acids, acrylamide, hydroxypropyl acrylate or vinylpyrrolidone, and (2) 2-acrylamide-2-methylpropane sulfonic acid or its sodium salt, sodium 2-acrylamide-2-methylpropane sulfonate. The copolymer has a weight average molecular weight of from about 1,000 to about 10,000.

The present invention also is directed to a novel slurry comprising calcium exotoxin and about 0.25 to about 2.5 percent by weight of such copolymer.

Among the several advantages of this invention, may be noted the provision of a method for concentrating calcium exotoxin slurries to higher degrees than conventionally attained without increasing the viscosity thereof to unmanageable levels; the provision of such method that does not result in unreasonably rapid fouling of ultrafiltration membranes employed for removal of water from the slurry; and the provision of a slurry that can be concentrated in such manner.

DETAILED DESCRIPTION OF THE PREFERRED EMBODIMENTS

In accordance with the present invention, it has been discovered that adding to a calcium exotoxin slurry a sufficient amount of a copolymer of certain simple vinyl-based monomers and 2-acrylamide-2-methylpropane sulfonic acid or its sodium salt, the copolymer having a weight average molecular weight of from about 1,000 to about 10,000, suppresses the viscosity of the slurry substantially, permitting the slurry to be concentrated to a significantly higher degree than possible conventionally without raising the viscosity of the slurry to unmanageable levels. Moreover, the addition of the copolymer does not significantly increase the rate of fouling of ultrafiltration membranes commonly used in such systems. These achievements are particularly surprising in that additives of somewhat similar chemistries have been found not to produce significant viscosity suppression.

The vinyl-based monomer is a monomer that includes the vinyl group, and may be written as $R_1R_2C{:}CR_3R_4$. Generally, $R_1$ is hydrogen and $R_3$ is hydrogen or methyl. Preferably, $R_2$ is hydrogen, but may be a relatively small organic moiety (about five or fewer, but typically about one or two, carbon atoms) such as a carboxyl group, and $R_4$ is a carbonyl group such as a carboxyl group, an amide-forming acyl group ($-CONH_2$), $-COOCH_2CHOHCH_3$ or a pyrrolidone group $$\left(-N\begin{array}{c}CH_2\\ \diagdown CH_2\\ |\\ CH_2\\ \diagup\\ C\\ \|\\ O\end{array}\right),$$

thus to form an acrylic-based monomer. Alkali metal, especially sodium, salts of the monomer acids also have been found to be suitable, although the acid forms have been found to be preferable because they are more reactive.

The vinyl-based monomer should be water soluble so that the copolymerization reaction can be carried out in an aqueous medium and aqueous slurries can be treated with the resulting copolymer. In view of this need for water solubility and the preference for the acid form and low cost, acrylic acid is the most desirable vinyl-based monomer, followed by methacrylic acid and then maleic acid and acrylamide. Of the sodium salts, sodium acrylate is most preferred, followed by sodium methacrylate.

The acid, 2-acrylamide-2-methylpropane sulfonic acid is referred to herein sometimes as AMPS and its sulfonate salt (for example, an alkali metal sulfonate, especially sodium sulfonate) as AMPS salt. AMPS salt has been found to form a block copolymer with the vinyl monomer, whereas AMPS forms a more random copolymer with the vinyl monomer. The more random types of copolymer, such as a Rohm and Haas product identified as Acrysol QR-1086 (see Rohm and Haas sales brochure CS-321a, dated December 1986, incorporated herein by reference), have been found to be more effective in viscosity suppression, especially if first neutralized such as with sodium hydroxide. AMPS has been found to be far more reactive than AMPS salt and so is preferred. However, if the copolymer is prepared from AMPS, the copolymer may contain up to 50 mole percent AMPS or more, while if the copolymer is prepared from AMPS salt, it may contain only on the order of 15 mole percent AMPS salt, especially if the copolymer is more random as opposed to a block copolymer. Because AMPS and AMPS salt are relatively expensive compared to the vinyl monomer, it is preferred to minimize the amount used. Thus, although AMPS is more reactive than AMPS salt, the salt has its advantages since a lower amount may be used. In either case, however, activity has been found to increase with increasing AMPS/AMPS salt concentration, with cost being a limiting factor. For example, of block copolymers tested with various AMPS concentrations from 5 to 50 mole percent, a block copolymer with an AMPS concentration of 50 mole percent was the most effective. On the other hand, with a random copolymer, an AMPS concentration of about 15 mole percent was found even more effective.

The copolymerization reaction is carried out by well known techniques as can be seen from the references to it in U.S. Pat. Nos. 3,928,196 to Persinski et al. and No. 4,552,665 to Ralston et al., both of which are incorporated herein by reference.

Thus, the copolymer formed between the vinyl monomer and AMPS or AMPS salt has a weight average molecular weight of from about 1,000 to about 10,000, preferably about 3,000 to about 10,000, such as about 4,500, and contains from about 5 to 50 mole percent AMPS or AMPS salt and from about 95 to about 50 mole percent vinyl monomer. It should be understood, however, that although the product is referred to as a "copolymer", the term "copolymer" is intended to include polymers such as an AMPS/acrylic acid/sodium acrylate polymer that might sometimes be referred to as terpolymers in that the acrylic acid and sodium acrylate technically are different monomers, albeit merely the corresponding acid and salt.

Neutralization of the copolymer has been found to improve its efficacy. It is believed that this is because the neutralization allows a complex to form between the copolymer and the protein in the medium treated. Moreover, the charge of the copolymer is believed to have an effect as well and so a higher pH product, such as a pH of from about 6 to about 7 is preferred. Thus, benefits may be derived by neutralizing the product such as with sodium hydroxide.

The method of this invention involves simply adding the copolymer to the calcium exotoxin slurry to be treated. Preferably, the copolymer is added while the viscosity of the slurry is still at manageable levels. The copolymer may be employed in an amount sufficient to suppress the viscosity of the slurry. Preferably, the copolymer is added in an amount to make up about 0.5 to about 2, preferably about 1 to about 1.5, weight percent of the treated slurry.

The following examples describe preferred embodiments of the invention. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims which follow the examples. In the examples, all percentages are given on a weight basis unless otherwise indicated.

EXAMPLE 1

A variety of additives were tested as viscosity-suppressing agents in a bioinsecticide calcium exotoxin slurry at 23° C. The additives were tested at a one percent concentration. The additives tested were as follows, where "% active" refers to the concentration of the identified chemistry in the additive and Mn refers to the number average molecular weight, as measured by GPC:

| Additive | Chemistry Type |
| --- | --- |
| A* | Acrylic acid/AMPS salt copolymer, 15 mole % AMPS salt, 25% active, Mn = 2410, pH = 6 to 7 |
| B* | Acrylic acid/AMPS salt copolymer, 15 mole % AMPS salt, 40% active, Mn = 2410, pH = 4.2 |
| C | Acrylic acid/AMPS/hydroxypropylacrylate terpolymer (molar proportion of 4.7:1:1) |
| D | Sulfate surfactant |
| E | Quaternary surfactant |
| F | Acrylic acid/AMPS salt copolymer, 5 mole % AMPS salt, 40% active, Mn = 1659, pH = 1.2 |
| G | Acrylic acid/AMPS salt copolymer, 8 mole % AMPS salt, 40% active, Mn = 925, pH = 2.49 |
| H | Acrylic acid/AMPS salt copolymer, 13 mole % AMPS salt, 40% active, pH = 2.64 |
| I | Acrylic acid/AMPS copolymer, 25 mole % AMPS, 40% active, Mn = 1609, pH = 1.81 |
| J | Acrylic acid copolymer sold as SOKALAN CP5 by BASF |
| K | Tridocyl sulfosuccinate sold as Aerosol TR-70 by American Cyanamid |
| L | Methacrylic acid/AMPS copolymer, 25 mole % AMPS, 40% active, Mn = 4704, pH = 1.22 |
| M* | Acrylic acid/AMPS copolymer, 50 mole % AMPS, 40% active, Mn = 2035, pH = 1.64 |
| N | Acrylic acid copolymer sold as SOKALAN CP7 by BASF |
| O | Acrylic acid copolymer sold as SOKALAN CP13S by BASF |

*Copolymers within the scope of the invention

The additives were added to each sample drop-wise by syringe to the media, which was agitated with a paddle prop mixer. The viscosity of the slurry was measured with a Brookfield Viscometer Model LVT, using spindle number 3 at 30 rpm. The results were as follows:

| Additive | Viscosity (cps) |
| --- | --- |
| None | 1,140 |
| A* | 340 |
| B* | 604 |
| C | 924 |
| D | 848 |
| E | 836 |
| F | over 1,000 |
| G | 952 |
| H | 936 |
| I | over 1,000 |
| J | 720 |
| K | 936 |
| L | 820 |
| M* | 472 |
| N | 921 |
| O | 890 |

*Copolymers within the scope of the invention.

EXAMPLE 2

Additive A of Example 1, above, was added to further samples of the slurry of Example 1 in various dosages. The tests were conducted at 10° C. and with spindle 1 of the viscometer. Otherwise, the tests were conducted as set forth in Example 1. The results were as follows:

| Dosage (% Concentration) | Viscosity (cps) |
| --- | --- |
| 0 | 965 |
| 0.25 | 872 |
| 0.50 | 696 |
| 1.00 | 444 |
| 1.50 | 212 |
| 2.00 | 188 |

What is claimed is:

1. A method for suppressing the viscosity of a calcium exotoxin slurry comprising calcium exotoxin bioinsecticide product, fermentation by-products, water, biomass and food nutrients, comprising adding to the slurry a viscosity-suppressing amount of a copolymer of (1) a vinyl-based monomer selected from the group consisting of acrylic acid, methacrylic acid, maleic acid, sodium salts of any of such acids, acrylamide, hydroxypropyl acrylate and vinylpyrrolidone and (2) 2-acrylamide-2-methylpropane sulfonic acid or its sodium salt, the copolymer having a weight average molecular weight of from about 1,000 to about 10,000.

2. A method as set forth in claim 1 wherein the vinyl-based monomer is an acrylic-based monomer selected from the group consisting of acrylic acid, methacrylic acid, maleic acid, the sodium salt of any of such acids, acrylamide and hydroxypropyl acrylate.

3. A method as set forth in claim 2 wherein the vinyl-based monomer is a water-soluble acrylic-based monomer selected from the group consisting of acrylic acid, methacrylic acid, maleic acid, the sodium salt of any of such acids and acrylamide.

4. A method as set forth in claim 3 wherein the acrylic-based monomer is selected from the group consisting of acrylic acid, methacrylic acid, maleic acid and the sodium salt of any of such acids.

5. A method as set forth in claim 4 wherein the acrylic-based monomer is selected from the group consisting of acrylic acid, methacrylic acid and the sodium salts of such acids.

6. A method as set forth in claim 5 wherein the acrylic-based monomer is selected from the group consisting of acrylic acid and its sodium salt.

7. A method as set forth in claim 6 wherein the acrylic-based monomer is the sodium salt of acrylic acid and the copolymer comprises about 85 mole percent units of the acrylic monomer.

8. A method as set forth in claim 6 wherein the acrylic-based monomer is acrylic acid and the copolymer comprises about 85 mole percent units of the acrylic monomer.

9. A method as set forth in claim 6 wherein the viscosity-suppressing amount is from about 0.25 to about 2.5 percent by weight of the slurry.

10. A method as set forth in claim 9 wherein the viscosity-suppressing amount is from about 1 to about 2 percent by weight of the slurry.

11. A method as set forth in claim 6 wherein the copolymer has a weight average molecular weight of from about 3,000 to about 10,000.

12. A calcium exotoxin slurry comprising calcium exotoxin bioinsecticide fermentation by-products, water, biomass, food nutrient and about 0.25 to about 2.5 percent by weight of a copolymer of (1) a vinyl-based monomer selected from the group consisting of acrylic acid, methacrylic acid, maleic acid, the sodium salt of any of such acids, acrylamide, hydroxypropyl acrylate and vinylpyrrolidone, and (2) 2-acrylamide-2-methylpropane sulfonic acid, the copolymer having a weight average molecular weight of from about 1,000 to about 10,000.

13. A slurry as set forth in claim 12 wherein the vinyl-based monomer is an acrylic-based monomer selected from the group consisting of acrylic acid, methacrylic acid, maleic acid, the sodium salt of any of such acids, acrylamide and hydroxypropyl acrylate.

14. A slurry as set forth in claim 13 wherein the vinyl-based monomer is a water-soluble acrylic-based monomer selected from the group consisting of acrylic acid, methacrylic acid, maleic acid, the sodium salt of any of such acids and acrylamide.

15. A slurry as set forth in claim 14 wherein the acrylic-based monomer is selected from the group consisting of acrylic acid, methacrylic acid, maleic acid and the sodium salt of any of such acids.

16. A slurry as set forth in claim 15 wherein the acrylic-based monomer is selected from the group consisting of acrylic acid, methacrylic acid and the sodium salts of such acids.

17. A slurry as set forth in claim 16 wherein the acrylic-based monomer is selected from the group consisting of acrylic acid and its sodium salt.

18. A slurry as set forth in claim 17 wherein the acrylic-based monomer is the sodium salt of acrylic acid and the copolymer comprises about 85 mole percent units of the acrylic monomer.

19. A slurry as set forth in claim 17 wherein the acrylic-based monomer is acrylic acid and the copolymer comprises about 85 mole percent units of the acrylic monomer.

20. A slurry as set forth in claim 17 wherein the copolymer has a weight average molecular weight of from about 3,000 to about 10,000.

* * * * *